United States Patent [19]
Rowden et al.

[11] Patent Number: 5,643,285
[45] Date of Patent: Jul. 1, 1997

[54] VAGINAL EXTENDER FOR COLPOTOMY SURGERY

[75] Inventors: Jimmy M. Rowden, Olathe, Kans.;
John E. Heaton, Kansas City, Mo.;
Charles H. Koh, Mequon, Wis.

[73] Assignee: Blairden Precision Instruments, Inc., Lenexa, Kans.

[21] Appl. No.: 324,656

[22] Filed: Oct. 18, 1994

[51] Int. Cl.⁶ ............................................. A61B 17/42
[52] U.S. Cl. ............................................. 606/119
[58] Field of Search .................................. 606/119, 193

[56] References Cited

U.S. PATENT DOCUMENTS

| | | |
|---|---|---|
| 1,856,295 | 5/1932 | Sovatkin . |
| 2,186,143 | 1/1940 | Neugass . |
| 2,456,806 | 12/1948 | Wolffe . |
| 3,131,690 | 5/1964 | Innis et al. . |
| 3,153,267 | 10/1964 | Rowland, Jr. . |
| 3,196,865 | 7/1965 | Rose . |
| 3,749,088 | 7/1973 | Gauther . |
| 3,766,909 | 10/1973 | Ozbey . |
| 3,877,433 | 4/1975 | Librach . |
| 3,948,270 | 4/1976 | Hasson . |
| 4,022,208 | 5/1977 | Valtchev . |
| 4,066,071 | 1/1978 | Nagel . |
| 4,323,057 | 4/1982 | Jamieson . |
| 4,430,076 | 2/1984 | Harris . |
| 4,562,832 | 1/1986 | Wilder et al. . |
| 4,597,030 | 6/1986 | Brody et al. . |
| 4,627,421 | 12/1986 | Symbas et al. . |
| 4,775,362 | 10/1988 | Kronner . |
| 4,996,974 | 3/1991 | Ciarlei . |
| 4,997,419 | 3/1991 | Lakatos et al. . |
| 5,104,377 | 4/1992 | Levine . |
| 5,209,754 | 5/1993 | Ahlluwalia ........................ 606/119 |
| 5,232,443 | 8/1993 | Leach . |
| 5,237,985 | 8/1993 | Hodgson et al. ................. 606/119 |
| 5,242,240 | 9/1993 | Gorham . |
| 5,273,026 | 12/1993 | Wilk . |

FOREIGN PATENT DOCUMENTS 2078526  6/1980  Germany .

Primary Examiner—Robert A. Hafer
Assistant Examiner—Benjamin Koo
Attorney, Agent, or Firm—Hovey, Williams, Timmons & Collins

[57] ABSTRACT

A colpotomy assembly (10) having a vaginal extender (20) and uterine manipulator (16) for use in performing various female pelvic surgeries, including laparoscopic hysterectomies, laparoscopically assisted vaginal hysterectomies, and other female pelvic laparoscopic procedures where removal of tissue specimens through a colpotomy incision is indicated.

12 Claims, 9 Drawing Sheets

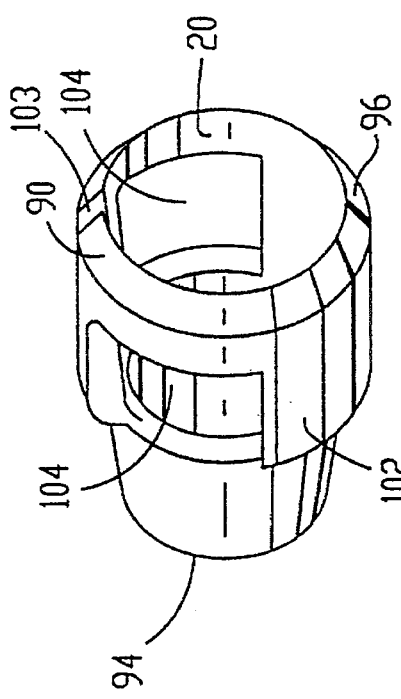
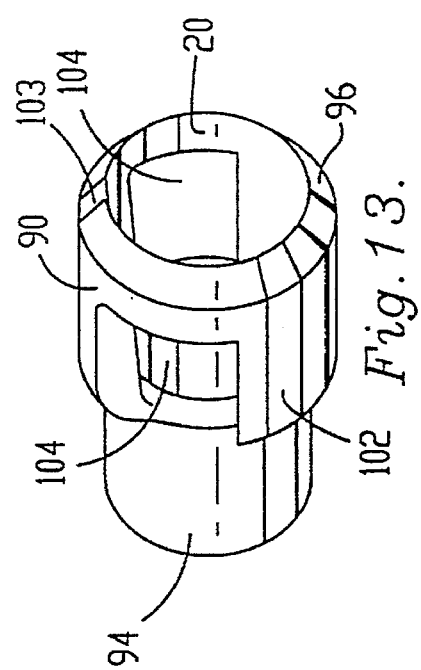
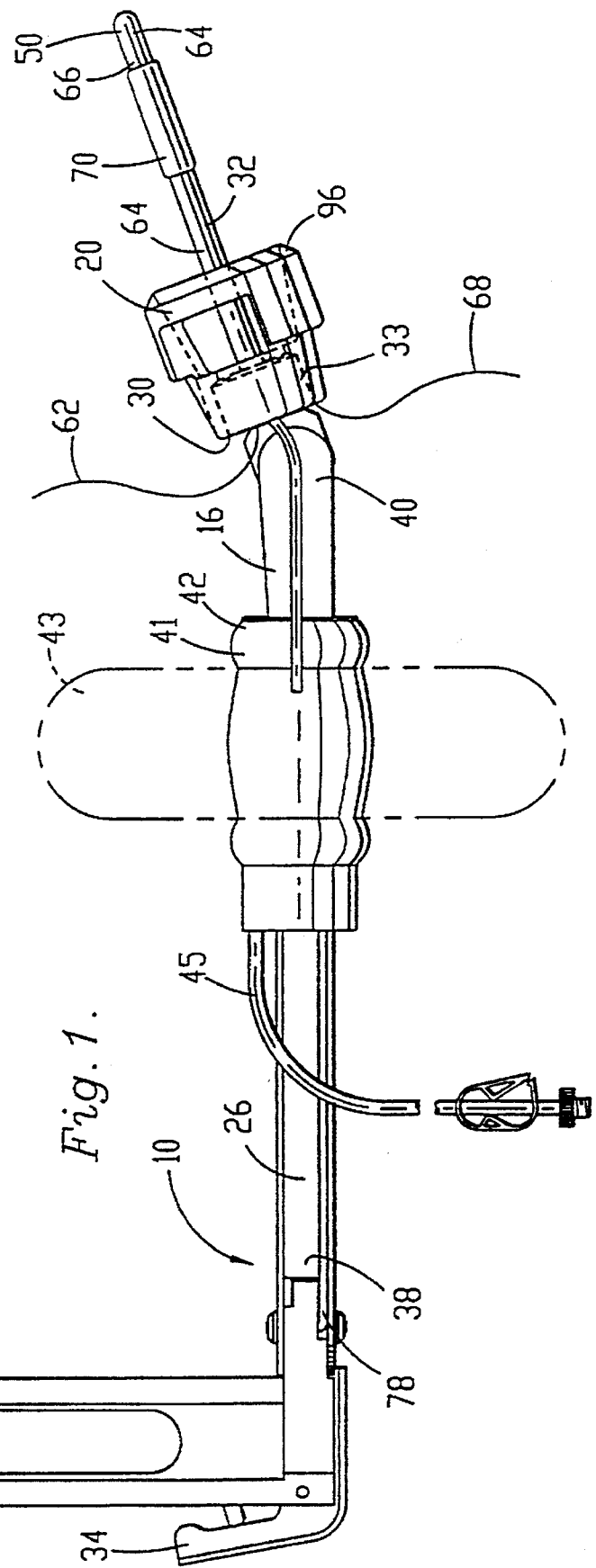
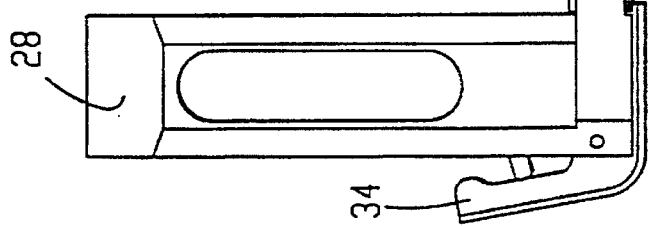

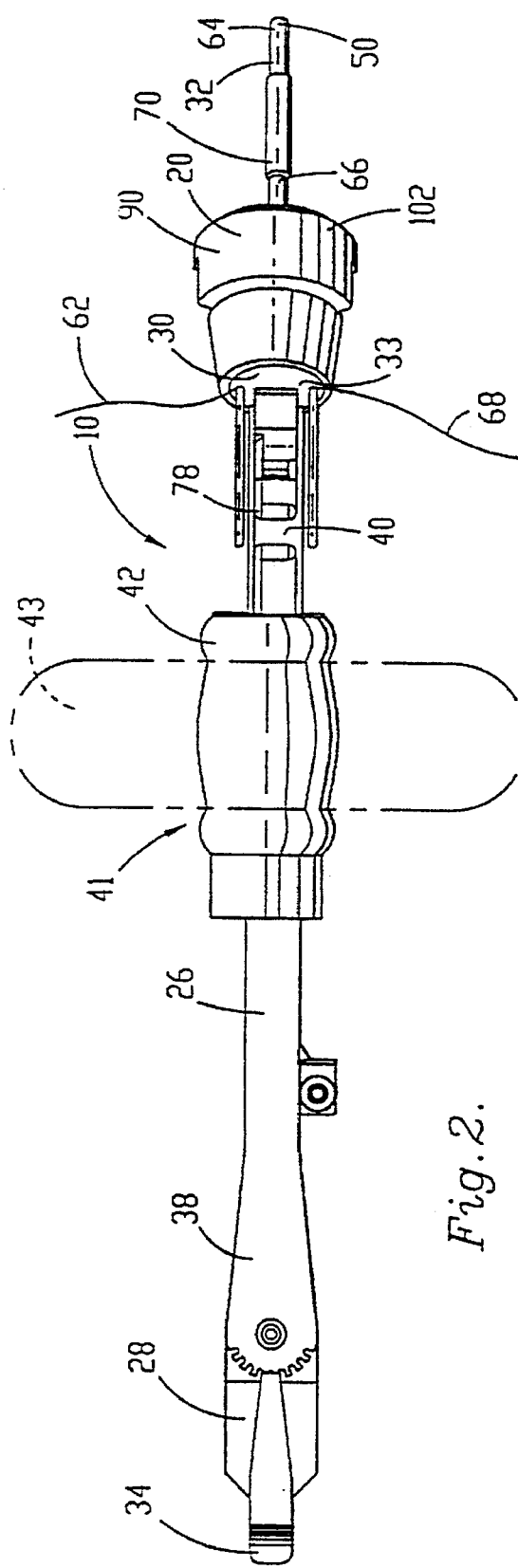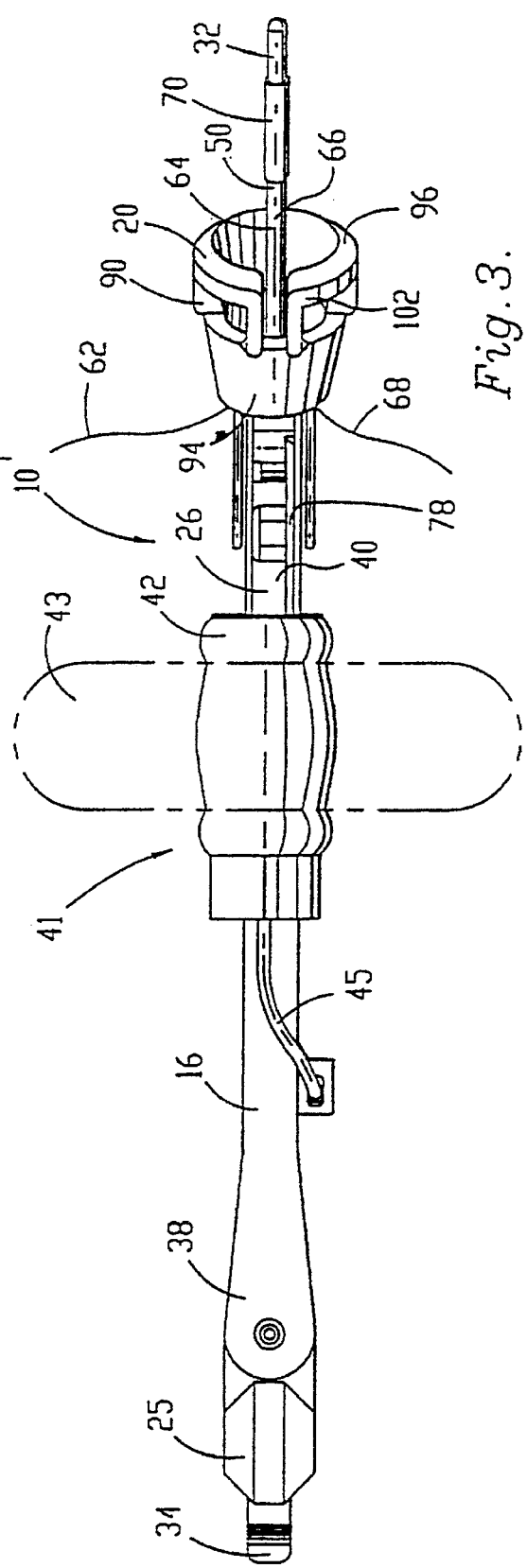

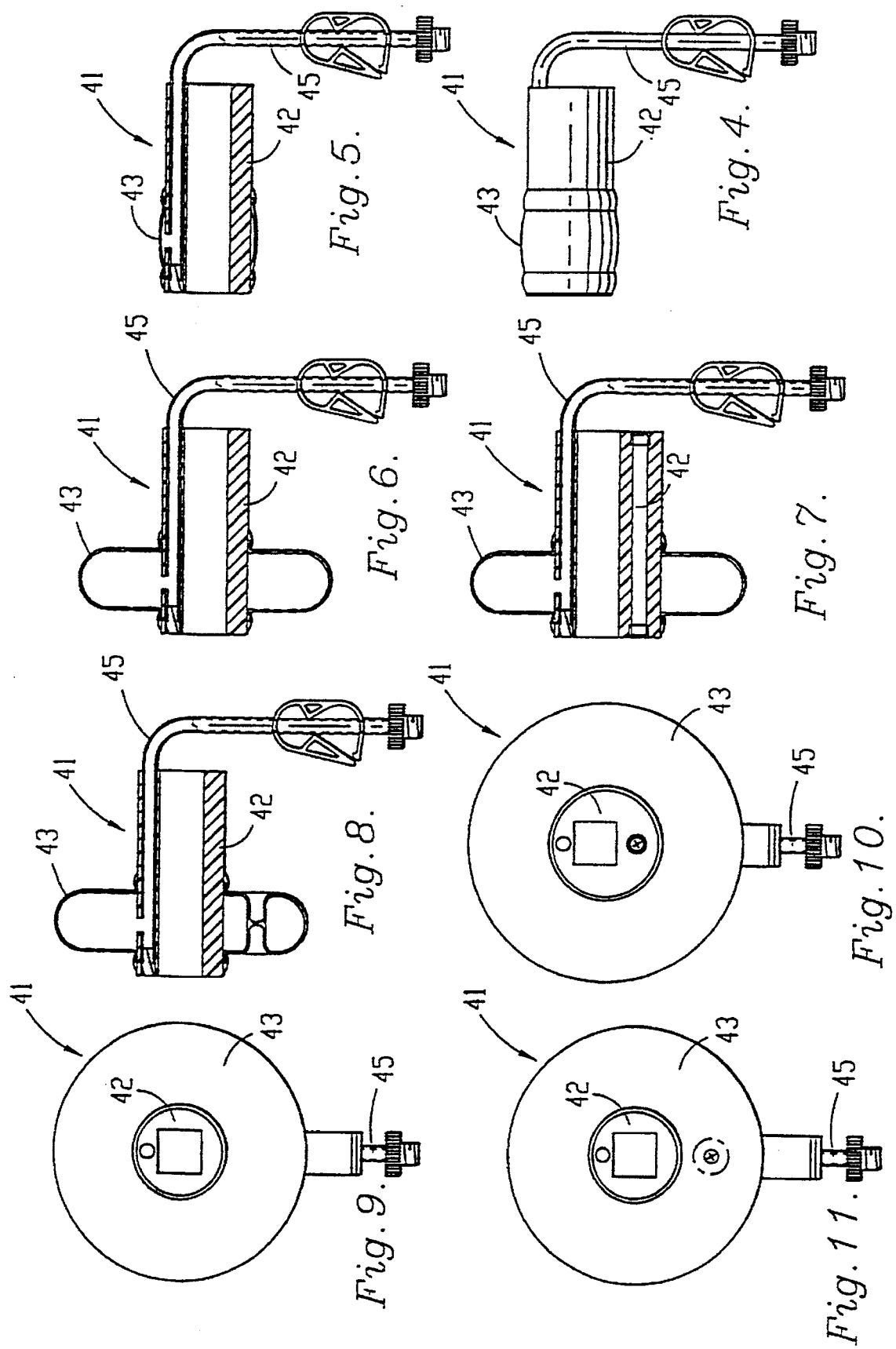

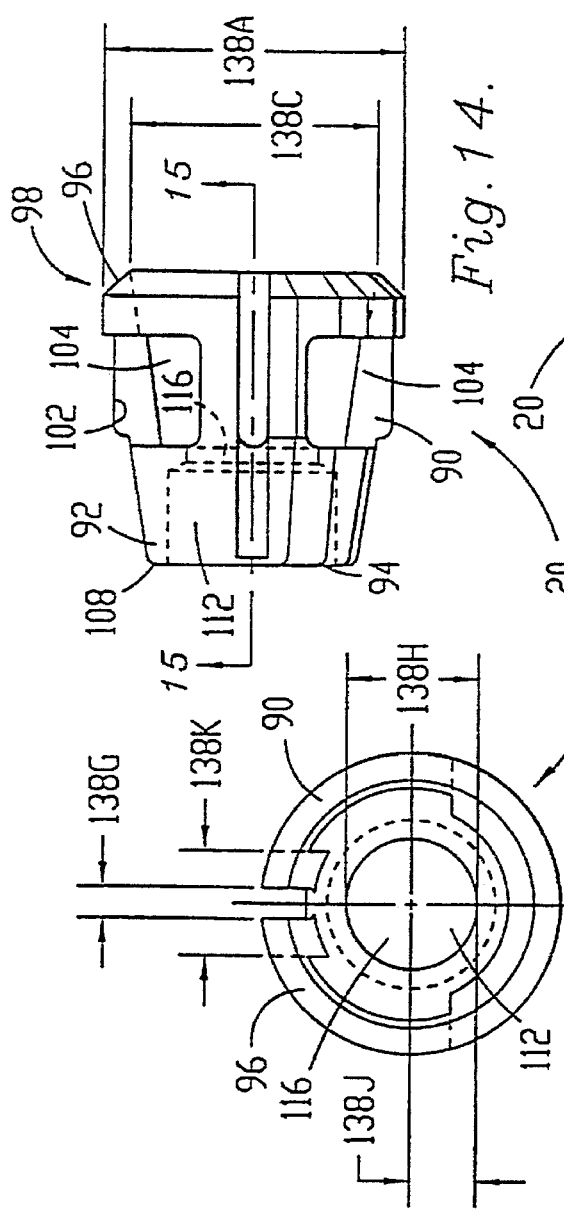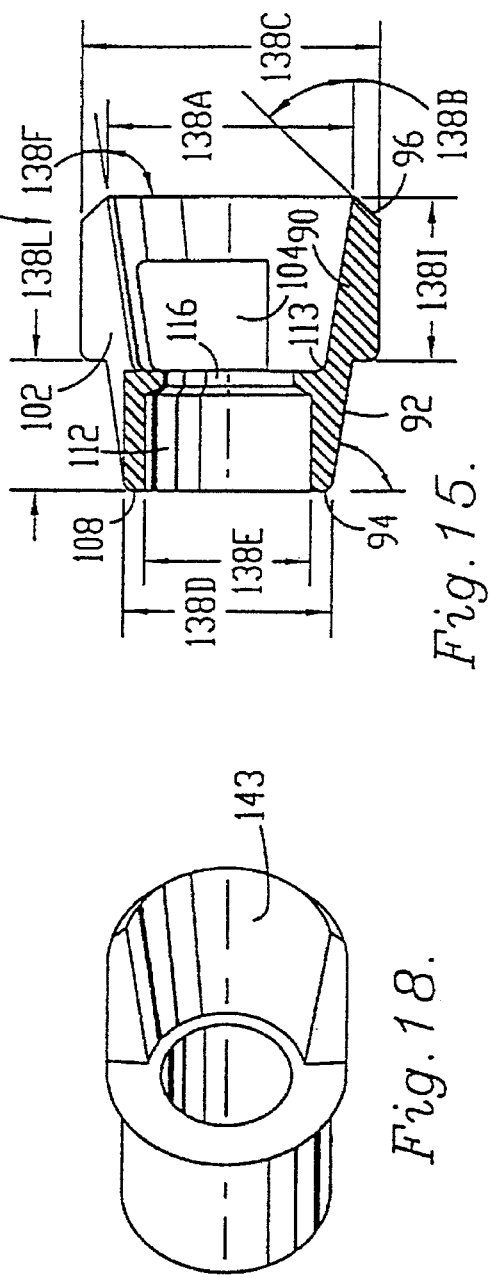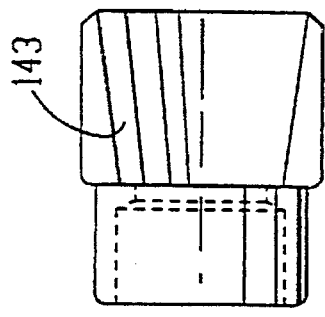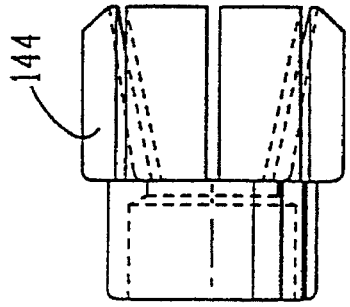

VAGINAL EXTENDER FOR COLPOTOMY SURGERY

BACKGROUND OF THE INVENTION

1. Field of the Invention

The present invention relates to a vaginal extender for use in performing various female pelvic surgeries, including laparoscopic hysterectomy, laparoscopically assisted vaginal hysterectomy, and other female pelvic laparoscopic procedures where removal of tissue specimens through a colpotomy incision is indicated.

2. Description of the Prior Art

Conventional hysterectomy surgical procedures typically involve one of four approaches—vaginal hysterectomy, total abdominal hysterectomy (TAH), total laparoscopic hysterectomy (TLH), and laparoscopically assisted vaginal hysterectomy (LAVH). Vaginal, TLH and LAVH have become more popular among surgeons because these approaches are less invasive than TAH, with TLH being the least invasive approach. TLH is less invasive than LAVH because it avoids the trauma normally caused by the expansion induced to the vaginal area to permit access of the surgeons hands to the cervical area. Unless medical indications require TAH (such as in the case of tumor removal and the associated need to avoid cell spillage), vaginal, TLH and LAVH are usually viewed as more preferable because each is less invasive when compared to major abdominal surgery. Thus, TLH and LAVH approaches usually result in shorter hospitalization and recovery times.

Difficulty, however, is encountered when employing vaginal, TLH and LAVH techniques due to inherent limitations on visibility, anatomical identification, and the ability to manipulate organs (especially the uterus). In the case of TLH, these limitations are particularly pronounced because of higher degree of difficulty in securing the uterine arteries and cardinal ligaments associated with this approach. A higher degree of surgical difficulty has been found empirically to give rise to an increased risk of inadvertent damage to or dissection into the bladder, ureters, uterine vessels and uterosacral and cardinal ligaments during the surgical procedure. Although the risk of inadvertent damage, for example, to the ureters can be minimized by the insertion of ureteral stints and/or peritoneal dissection to delineate ureter location, such techniques increase the complexity and the cost of the hysterectomy.

Other limitations associated with vaginal, TLH and LAVH surgical approaches, when compared to TAH, include limited exploratory ability and surgical control. Vaginal, TLH and LAVH approaches can also result in the unnecessary shortening of the vagina due to the limitations discussed above.

These difficulties and limitations have slowed the move by surgeons to use of the least invasive surgical approach (i.e., TLH), leading most gynecologists to perform LAVH.

Accordingly, there is a real and unsatisfied need in the surgical arts for a simplified total laparoscopic hysterectomy procedure to accurately secure uterine vessels and cardinal/uterosacral ligaments and to provide for a simplified colpotomy incision without ureteral dissection.

SUMMARY OF THE INVENTION

The present invention overcomes the problems outlined above, and provides a surgical method and assembly allowing accuracy, reproducibility and safety in performing the more challenging portion of a total laparoscopic hysterectomy. In particular, the present invention overcomes the problems outlined above by providing anatomical landmarks and colpotomy incision backstops within the female pelvic cavity to assist physicians and surgeons with visibility and to facilitate incisions that avoid damage to other structures, such as bladders and ureters, and that optimize vaginal length following a hysterectomy. Benefits that accrue in the practice of the instant invention include the preservation of the vaginal length by minimizing unnecessary excision vaginal tissue and non-division of uterosacral ligaments (with innervation intact and support of the vagina intact). The benefits associated with the instant invention may also accrue in connection when the instant invention is practiced in connection with a TAH.

A colpotomy assembly is provided for use with a simplified total laparoscopic hysterectomy procedure in the form of a colpotomy assembly including an elongated shaft member having a shaft handle mounted in pivotal relationship to a shaft proximal end and a vaginal extender mounted to a distal end of the shaft, the vaginal extender operatively coupled to the shaft handle for articulation of the vaginal extender relative to the frame. The vaginal extender includes structure for engaging a patient's vaginal fornix to provide an anatomical landmark and incision backstop for making colpotomy incisions from a patient's abdominal cavity. The vaginal extender is configured so that when employed by a surgeon during a hysterectomy procedure, the-fornix-engaging structure bears against at least a portion of a patient's vaginal fornix apex to permit a vaginal incision during a hysterectomy that optimizes vaginal length.

In the preferred embodiment, the vaginal extender is in the form of an annular main body having a proximal end integral with a cervix-engaging base and extending distally therefrom and presenting a substantially continuous circular, beveled fornix-engaging rim. The rim is configured to provide the anatomical landmark and incision backstop when inserted for use in a hysterectomy procedure. In alternative embodiments, the vaginal extender is provided with viewing windows disposed on and extending through the outer peripheral cylindrical surface to assist with the mounting of the extender on a patient's cervix so that proper contact is made with the patient's vaginal fornix apex and cervix.

BRIEF DESCRIPTION OF THE DRAWINGS

FIG. 1 a side elevational view showing a colpotomy assembly with a vaginal extender mounted on a uterine manipulator and tip.

FIG. 2 is a bottom plan view of the colpotomy assembly.

FIG. 3 is top plan view of the colpotomy assembly.

FIG. 4 is a side plan view of the vaginal occluder.

FIG. 5 is a cross-sectional, elevational view of the vaginal occluder showing the fluid conduit and balloon cuff uninflated.

FIG. 6 is a side, cross-sectional elevational view of the vaginal occluder showing the balloon inflated.

FIG. 7 is a side, cross-sectional elevational view of an alternative body of the vaginal occluder showing a surgical instrument access port extending through the occluder main body.

FIG. 8 is a side, cross-sectional elevational view of an alternative body of the vaginal occluder showing a surgical instrument access port disposed in the balloon cuff portion.

FIG. 9 is a front elevational view of the vaginal occluder showing the cuff inflated.

FIG. 10 is a front elevational view of the alternative embodiment of the occluder with the cuff inflated and showing the surgical instrument access port disposed in the occluder main body.

FIG. 11 is a front elevational view of the alternative embodiment of the occluder with the cuff inflated and showing the surgical instrument access port disposed in the inflated balloon cuff.

FIG. 12 is an enlarged, perspective elevational view of the vaginal extender.

FIG. 13 is an enlarged, perspective elevational view of an alternative embodiment of the vaginal extender.

FIG. 14 is an enlarged, side elevational view of the vaginal extender.

FIG. 15 is an enlarged, side cross-sectional view of the vaginal extender taken along line 15—15 in FIG. 14.

FIG. 16 is a top plan view of the vaginal extender.

FIG. 17 is a side elevational view showing the half-cup vaginal extender alternative embodiment.

FIG. 18 is an enlarged, top plan view of the half-cup vaginal extender alternative embodiment.

FIG. 19 is a perspective view of the finger vaginal extender alternative embodiment.

DETAILED DESCRIPTION OF THE PREFERRED EMBODIMENT

Description of the Colpotomy Assembly

Figure 21:
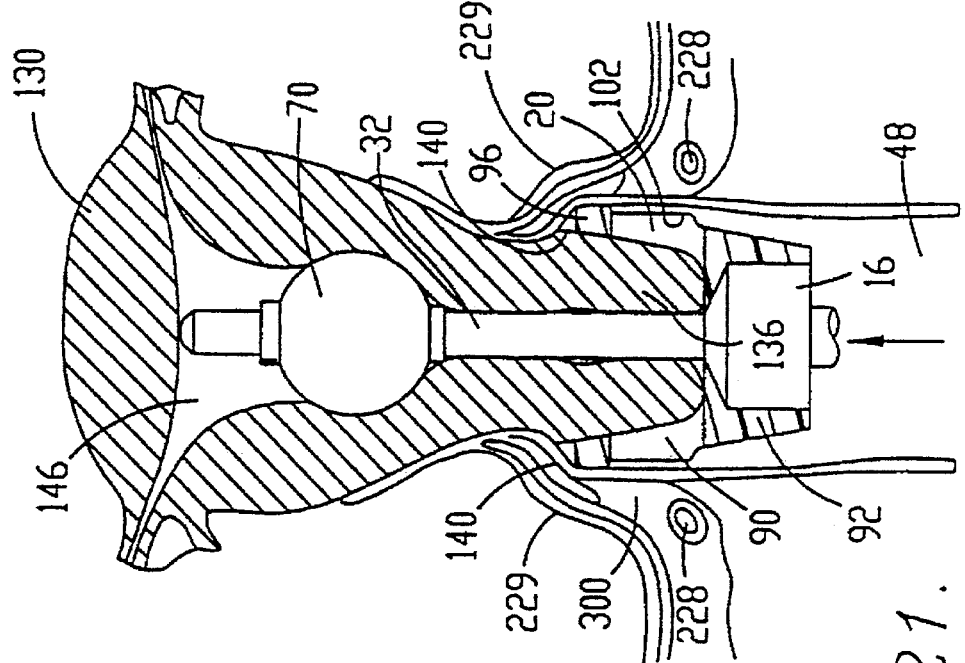
FIG. 21 is an anterior, cross-sectional view of a uterus showing the vaginal extender inserted and extended into the vaginal fornix apex following the cephalad push.
Figure 20:
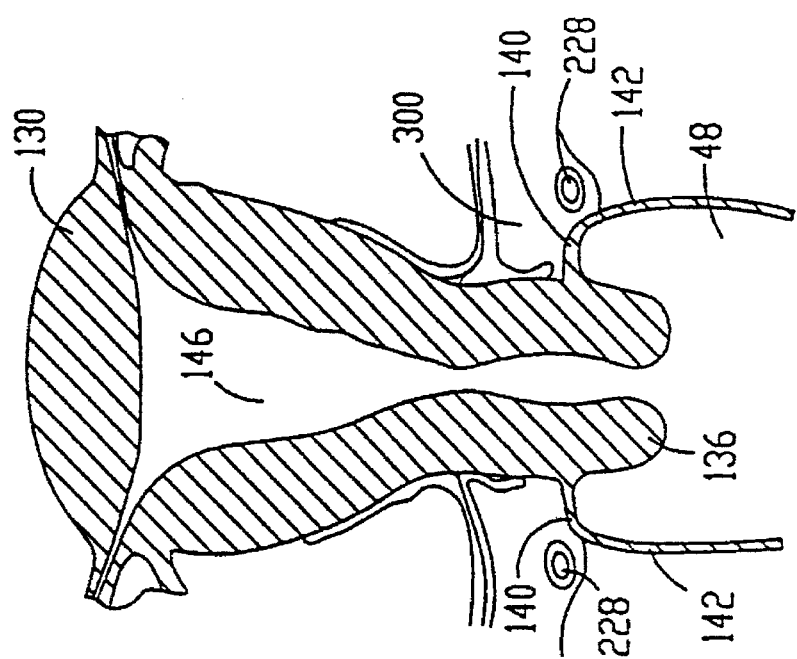
FIG. 20 is an anterior, cross-sectional view of a uterus.

Referring now to the drawings, the colpotomy assembly 10 used in the practice of the instant invention includes a uterine manipulator 16 and a vaginal extender 20.

Uterine manipulator 16 may be any uterine manipulating device known in the art, and in the preferred embodiment is a Rumi™ uterine manipulator (Blairden Precision Instruments, Inc., Lenexa, Kans. 66219). As shown in FIGS. 1–3, uterine manipulator 16 includes an elongated frame 26, a handle 28, a tip mount 30 configured to be removable, a uterine manipulating tip 32 and base 33, and a locking mechanism 34. The frame 26 defines a proximal end 38 and a distal end 40. A vaginal occluder 41 is slidably received by frame 26 and includes a main body 42 including an outwardly presented balloon cuff 43. A fluid conduit 44 is affixed to balloon cuff 43 through which fluid flows to balloon cuff 43 for inflation. In the preferred embodiment, occluder 41 is constructed of a medical grade silicone suitable for injection molding. Occluder 41 may also be provided with an access port 45 and is configured to permit the insertion of surgical tools therethrough.

Handle 28 is affixed in pivotal relationship to the frame proximate end 38. The tip mount 30 is affixed in pivotal relationship to the frame distal end 40. It will be appreciated that distal end 40 is configured to be inserted into the vaginal cavity 48 of a patient during use of the manipulator 16 in the course of examination or surgery, while the proximate end 38 remains exterior to the patient's body.

The tip 32 includes a natural or synthetic rubber body 50 (as used herein, the term "synthetic rubber" is intended to include within its meaning silicone compounds) with dye conduit 62 communicating with a tip bore 64 extending through finger 66. The tip also includes a balloon conduit 68 to communicate with an expandable balloon 70 surrounding the finger 66.

The uterine manipulator 16, in the preferred embodiment, also includes a locking mechanism 34 which serves to connect and fix handle 28 relative to frame 26. Connecting structure 78 operatively couples tip mount 30 to handle 14.

The vaginal extender 20 includes an annular main body 90 and includes a base 92 at its proximal end 94 and a fornix-engaging, circular rim 96 at its distal end 98. Circular rim 96 is beveled, as shown in FIGS. 14–19, to permit an anatomical landmark and incision backstop during use. Vaginal extender 20 is formed of any medical grade plastic material commonly known to those skilled in the art and obtainable from conventional suppliers. The extender 20 may alternatively be formed of any material of construction suitable for the use described below, including stainless steel or a rigid gauze composite. The annular body 90 presents an outer peripheral, generally cylindrical surface 102 which extends between the-fornix-engaging rim 96 and base 92. A laterally-extending slot 103 is positioned on the cylindrical surface 102 to permit use of surgical instruments as later explained.

Viewing windows 104 may be disposed in and extend through extend through the outer cylindrical surface 102, as shown in FIG. 13.

Base 92 includes a proximate end 108 presenting socket 112 for captively receiving the uterine manipulator tip base 33. Base 92 further includes a floor portion 113 having an aperture 116 extending therethrough between socket 112 and the annular main body 90 for receiving manipulator tip 32 when vaginal extender 20 is mounted on uterine manipulator 16, as shown in FIGS. 14–16. Aperture 116, in an alternative embodiment, has a diameter significantly larger than that associated with tip 32 (but smaller than the diameter associated with socket 112) to provide a view of the cervix 136 for situations where the extender 20 is placed into position before the uterine manipulator 16 is inserted into the uterus 130.

When vaginal extender 20 is mounted on the uterine manipulator 16, manipulator tip 32 extends axially through annular body 90, as shown in FIG. 1.

The dimensions of the vaginal extender 20, in the preferred embodiment, will now be described. Referring to FIGS. 14–16, the inner diameter 138a is between 0.99 inches and 1.18 inches, depending on anatomical indications. Rim 96 has a beveled angle 138b of 42 degrees. The outer diameter 138c of the annular main body 90 is about 1.246 inches to 1.436 inches, depending upon anatomical indications. The outer diameter 138d of base end 108 is about 1.0 inch. The inner diameter 138e of socket 112 is about 0.79 inches. The taper angle 138f of the interior surface 139 of annular main body 90 is about 99 degrees. The width 138g of lateral slot 103 is about 0.156 inches. The internal diameter 138h of aperture 116 is about 0.63 inches. The length 138i of annular main body 90 is about 0.815 inches. Referring to FIG. 19, the reference dimensions 138j and 138k associated with windows 104 are 0.187 inches and 0.50 inches, respectively. The depth 138m of socket 112 is 0.450 inches. The taper angle 138m of the base 92 is between 81 degrees and 90 degrees depending on anatomical indications.

Although specific dimensions are disclosed above for one of the preferred embodiments of the vaginal extenders 20, other factors may indicate the need for different shapes and sizes.

Insertion of the colpotomy assembly 10 into the vaginal cavity 48 with tip 32 inserted into the uterus 130 is largely similar to the procedures well known in the prior art for the insertion of uterine manipulators. A tenaculum can be used to aide the insertion of tip 32 into the uterus 130 by placing tip 32 into slot 103 during use. FIGS. 21, 22, 25 and 29 illustrate the colpotomy assembly 10 after it has been inserted for use in the practice of the instant invention. When inserted, cervix 136 is received into the annular main body 90 of the vaginal extender 20 and rim 96 is placed into engaging relationship with the apex 140 of fornix 142. Windows 104 are provided in the vaginal extender 22 to permit the viewing of the cervix 136 during the engagement of the vaginal extender 20 with cervix 136 and vaginal fornix apex 140. Uterine manipulator tip 132 is fully inserted in the uterus 130 and balloon 70 is inflated to come into engaging relationship with the uterus interior surface 146.

A vaginal extender 20 may have any shape or dimension suitable for use during hysterectomies involving colpotomy incisions provided that its shape and dimension is sufficient to delineate the anatomical landmarks and to provide incision backstops so that the surgical procedure will be simpler and safer and result in optimal vaginal length following the hysterectomy. Examples of alternative embodiments of extender 20 are shown in FIGS. 13, 16–18. Shown in FIG. 13 is a vaginal extender 20 with a base 92 having an outer peripheral surface which is cylindrical rather than tapered. Shown in FIGS. 17 and 18 is a "half-cup" vaginal extender 143. Shown in FIG. 19 is a finger vaginal extender 144. Extenders 143 and 144 are used in ways substantially identical to those described for vaginal extender 20. However, the particular shapes of extenders 143 and 144 may be indicated or otherwise advantageous based upon the anatomy of a particular patient.

Once the colpotomy assembly 10 is inserted into the vaginal cavity 48, the occluder 41 may be inflated to seal the distal vaginal cavity 150 from the proximal vaginal cavity 152. In the preferred embodiment, occluder 41 is inflated with sterile, water-based fluid because the preferred, silicone-based material of construction of the occluder cuff 43 is gas permeable. However, in applications where gas leakage from occluder 41 can be tolerated, air can be used to inflate cuff 43.

Figure 23:
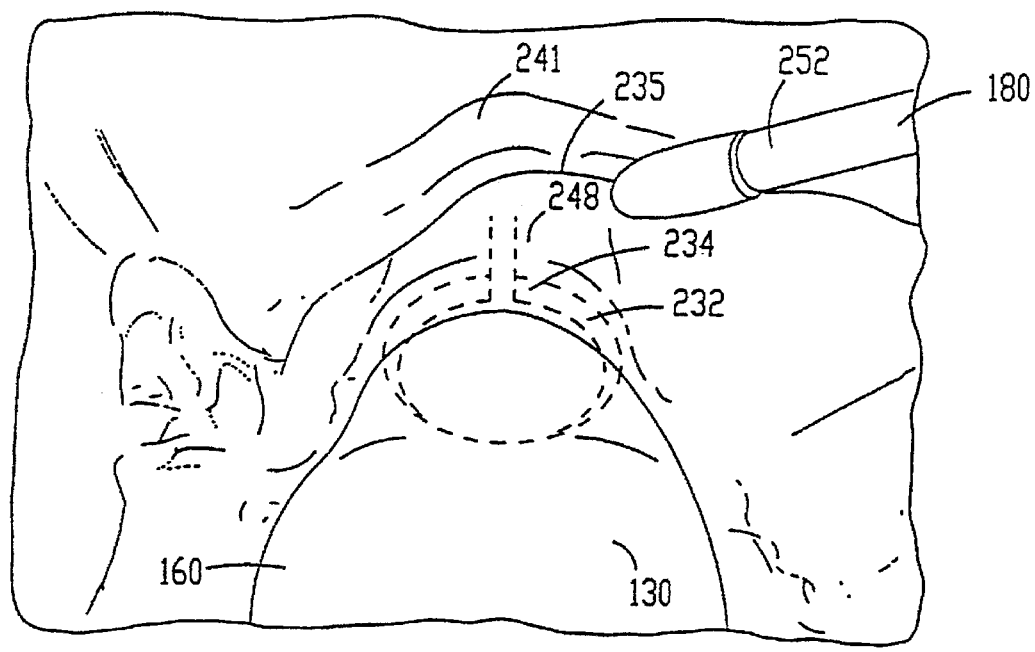
FIG. 23 is a frontal view of the retroverted uterus in the abdominal cavity.
Figure 24:
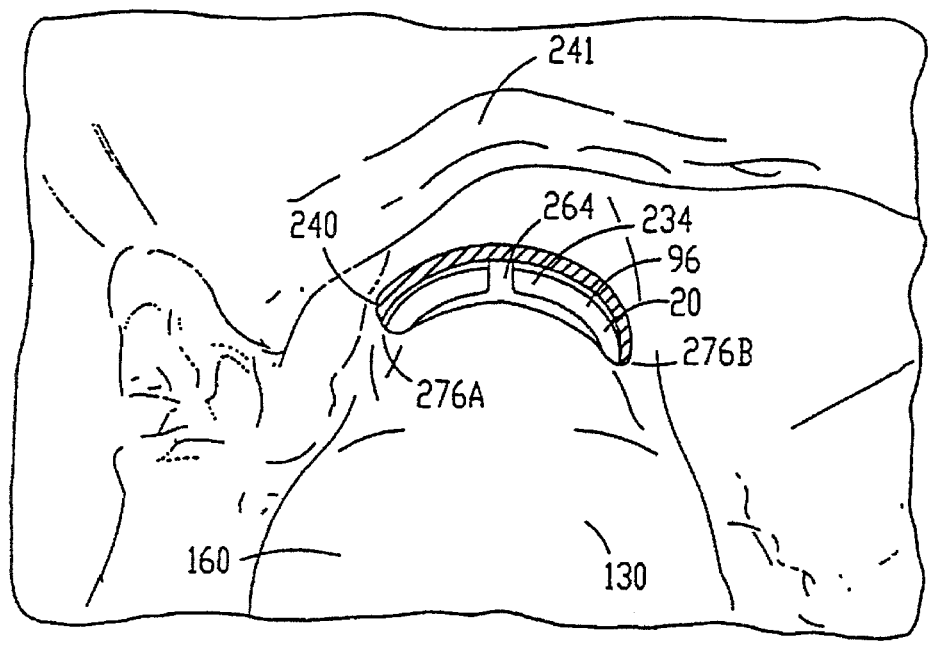
FIG. 24 is a frontal view of the retroverted uterus in the abdominal cavity showing the anterior rim portion.
Figure 22:
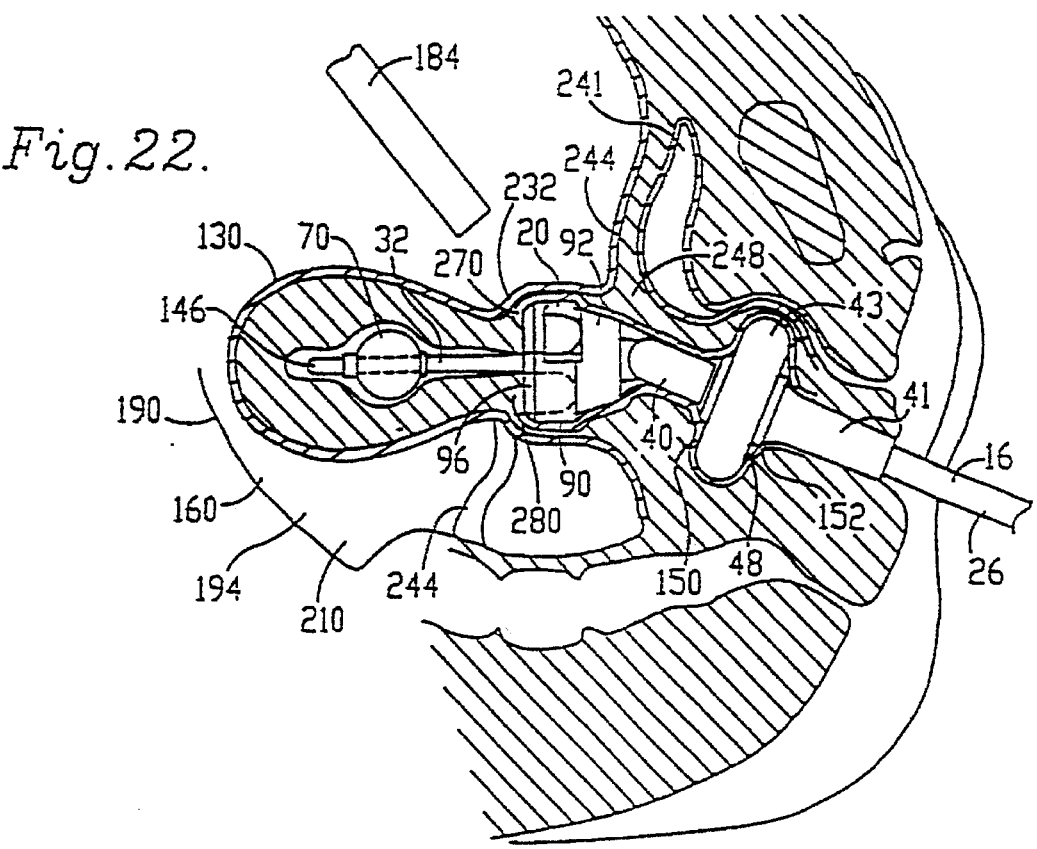
FIG. 22 is a cross-sectional, side view of the pelvic cavity showing the colpotomy assembly holding the uterus in an retroverted position.
Figure 25:
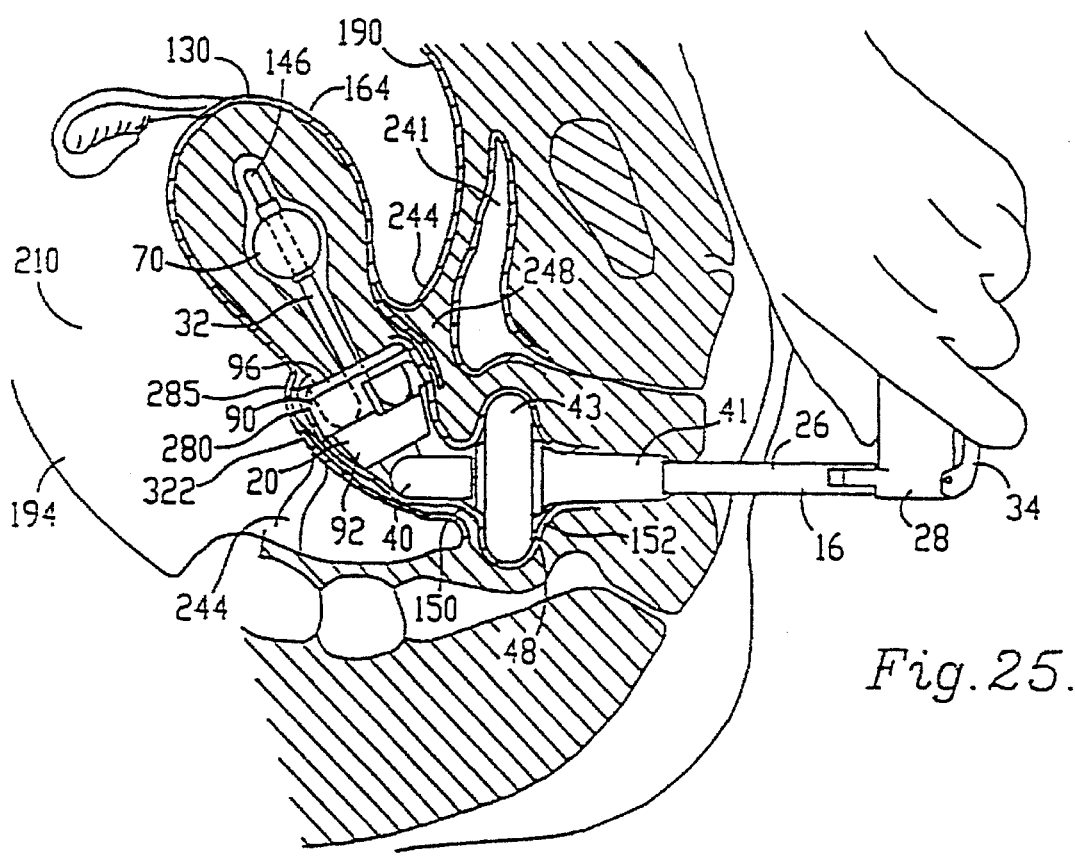
FIG. 25 is a cross-sectional, side view of the pelvic cavity showing the colpotomy assembly holding the uterus in an anteverted position.
Figure 26:
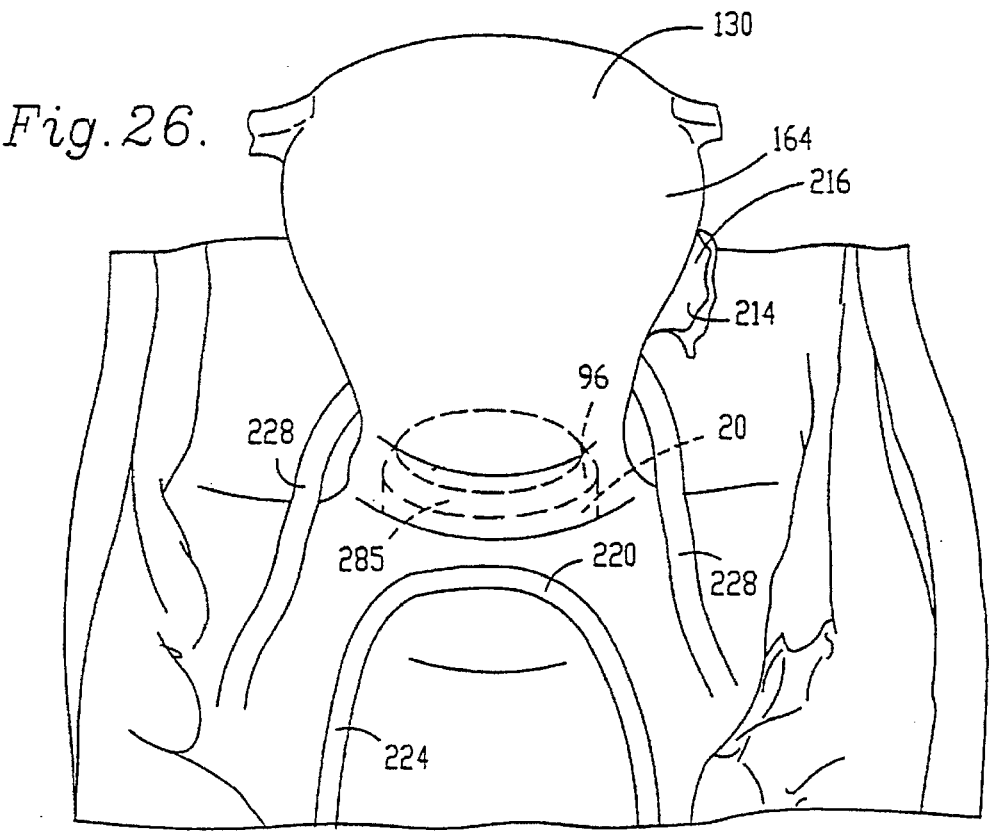
FIG. 26 is a frontal view of the anteverted uterus in the abdominal cavity.
Figure 27:
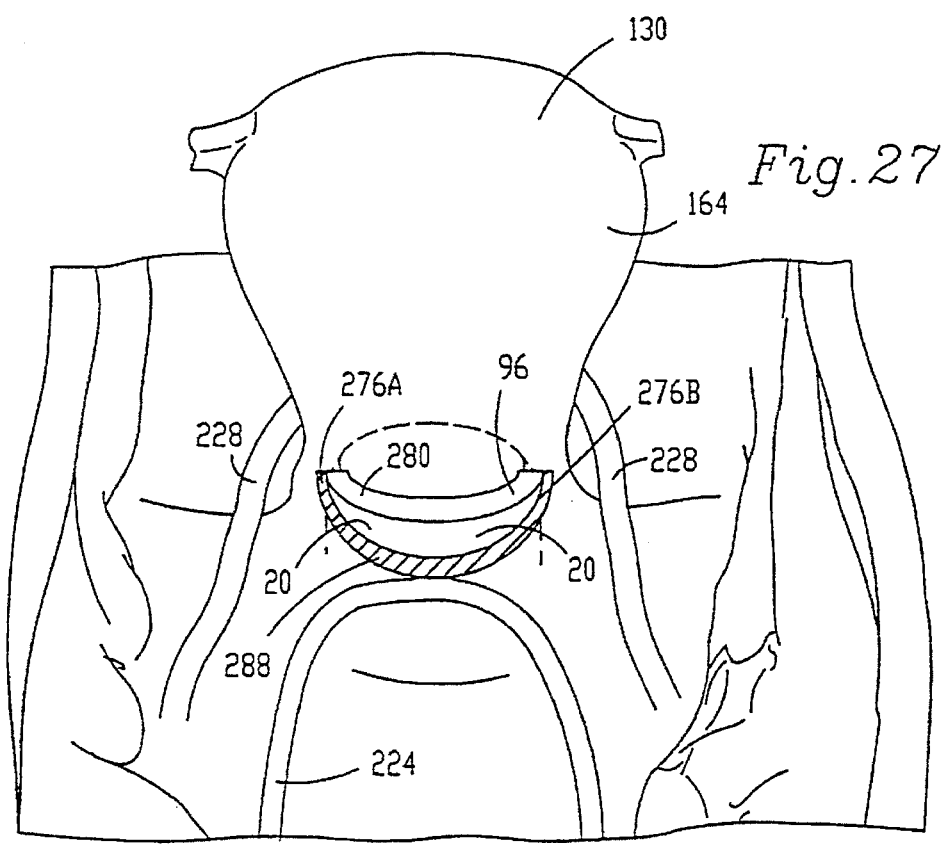
FIG. 27 is a frontal view of the anteverted uterus in the abdominal cavity showing the posterior rim portion.
Figure 28:
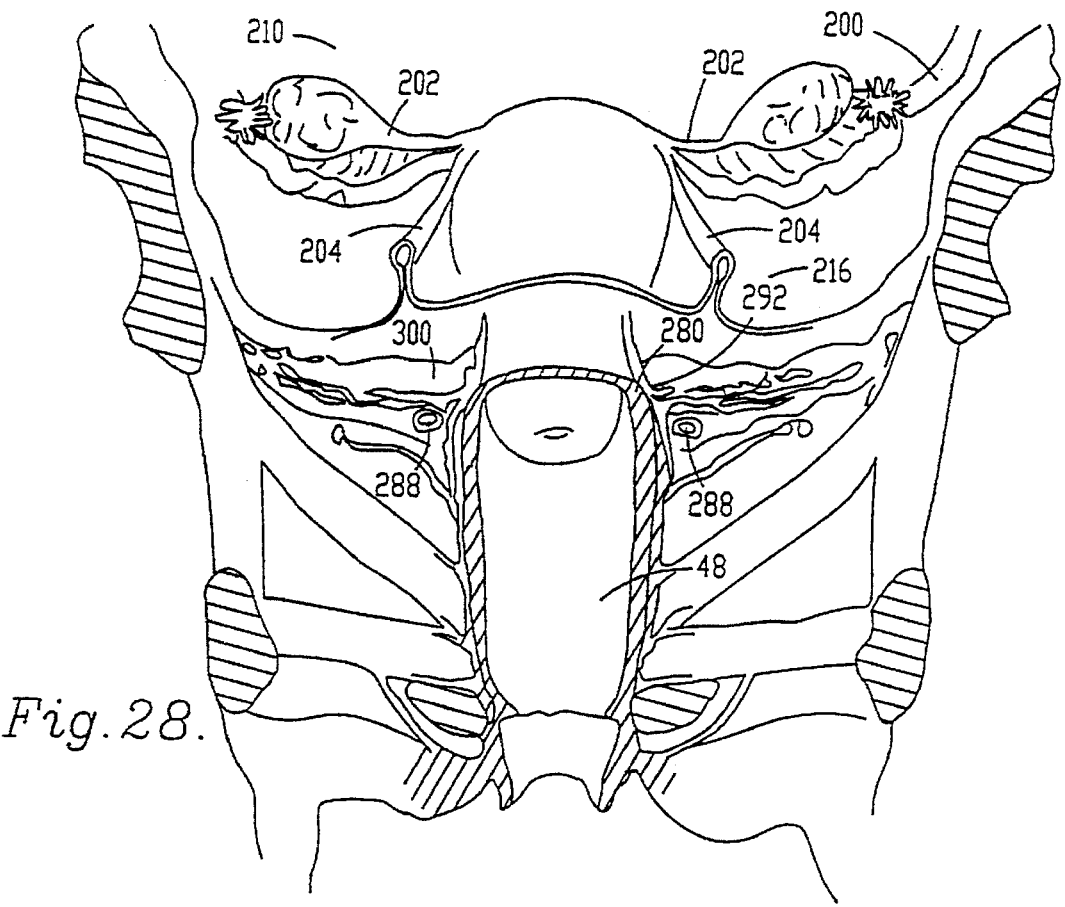
FIG. 28 is a cross-sectional view of a female pelvic cavity showing the position of various ligaments, blood vessels and ureters.

When a surgeon or physician desires to manipulate the uterus into a retroverted position, he simply articulates handle 28 in relation to frame 26 in the appropriate rotational direction. Articulated rotation of handle 28 causes the tip base 33, the uterine manipulator tip 32, and the vaginal extender 20 mounted thereto, to articulate and pivot in relationship to frame 26, placing uterus 130 in a retroverted position 160, as shown in FIGS. 22–24. To manipulate the uterus into an anteverted position 164, the surgeon or physician articulates handle 28 in the opposite rotational direction, which articulated rotation causes a corresponding articulated rotation of tip base 33, uterine manipulator tip 32, vaginal extender 20, and the engaged uterus 130, which moves uterus 130 into the anteverted position 164, as shown in FIGS. 25–27. The locking mechanism 34, if provided, serves to prevent undesired return of the uterus 130.

Description of the Simplified Total Laparoscopic Hysterectomy Method Employing Colpotomy Incisions The simplified total laparoscopic hysterectomy (TLH) method of the instant invention will now be described. A patient is prepared for TLH surgery according to procedures which are well known in the surgical arts and will not be repeated here. Once prepared, the abdominal cavity is inflated to facilitate the accessibility to and visibility of the female pelvic organs. Surgical instruments 180, including a laparoscope 184, are inserted through the abdomen wall 190 into the abdominal cavity 194.

A uterine manipulator, such as the colpotomy assembly 10 described above, is inserted into the vaginal cavity 48, as shown in FIGS. 21, 22, 25 and 29.

Upper Pedicles

The tubo-ovarian pedicle and suspensory ovary ligaments 200, proper ovarian ligaments 202, and round ligaments 204, are divided either medial or lateral to the ovary depending on whether oophorectomy is indicated, using a variety of energy sources, for example, bipolar, desiccation, stapler cutter, suture, endo-loop, as appropriate. The round ligament 204 is most conveniently bipolar desiccated and divided and allows the opening of the parametrial space 210. At this point, the posterior leaf 214 of the broad ligament 216 is divided by scissors or unipolar cautery down towards the immediate lateral aspect 220 of the uterosacral ligament 224. This division will allow lateral mobilization of the ureters 228.

Uterovesical Peritoneum

The colpotomy assembly 10 is adjusted to position the uterus 130 in a retroverted position 160 making the vaginal extender 20 easily visible. A cephalad (toward the head) push on the colpotomy assembly 10 causes further tenting 229 of the vaginal fornix 142, as shown in FIG. 21. A first anatomical landmark and incision backstop 232 is provided by anterior rim portion 234 of the rim 96 of vaginal extender 20 indicates the area of loose uterovesical peritoneum 138 where the incision 240, to reflect the bladder 241, will begin. The incision is performed again using scissors (or other dissecting tools), with unipolar or bipolar hemostasis as infrequently needed. The bladder peritoneum 244 is then elevated with a grasper 180 and the areolar tissue 248 may be pushed down towards the vagina against the anterior of main body 90 of the vaginal extender 20, using a Kittner 252. Alternatively, a sharp dissection will be made with the use of scissors cutting and dissecting the correct plane in the pubocervical fascia 256, which is avascular. It will now be easy to push the bladder 241 down some 2 cm from the vaginal fornix apex 140. The bladder 241 may be temporarily filled a this stage with methylene blue to indicate its position and intactness. The bladder pillars (not shown) may be laterally bipolar desiccated or unipolar divided, and further lateral reflection of the bladder 241 in a caudal direction is performed, using the Kittner 252. The lateral reflection of the bladder 241 in the caudal direction has the effect of pushing the ureters 228 laterally and inferiorly, aided by the previously divided posterior leaf 214 of the broad ligament 216.

Anterior Colpotomy

After positioning the uterus 130 in the retroverted position 160 and making a cephalad push of the colpotomy assembly 10 against the uterine cervix 136, an anterior colpotomy incision 264 is made over the anatomical landmark and incision backstop 232 provided by anterior portion 234 of rim 96. The anterior incision 264 is made using a unipolar electrode or other form of energy. The fornix-engaging rim 96 allows an accurate incision into the anterior vaginal fornix 270. The anterior colpotomy incision 264 extends laterally short of the lateral vaginal angle 276 on both sides 276A and 276B, as shown in FIG. 24.

The presence of the anatomical landmark and incision backstop 232 provided by the colpotomy assembly 10 ensures that dissection of the vagina 280 and parametrium 284 is accurate and does not proceed more caudal than is necessary. This is often the case where the apparatus and method of the instant invention is not employed because of the distorted visualization at laparoscopy and the inability to determine the location of the vaginal fornix apex 140.

The vaginal occluder 41 prevents the escape of gas used to inflate the abdominal cavity 194 during and following the first of any colpotomy incision, which, in the preferred practice, is the anterior colpotomy incision 264.

Posterior Colpotomy

The uterus 130 is now repositioned into the anteverted position 164 so that the fornix-engaging rim 96 is easily visible and palpable. The fornix apex 140 is now above the insertion of the uterosacral ligament 224. Therefore, it is not necessary to divide the uterosacral ligament 224 in order to perform a posterior colpotomy, thereby preserving existing uterine support and innervation and minimizing the bleeding that follows uterosacral transection. Furthermore, the ureters 228 are not endangered by division of the uterosacral ligament 224. A second anatomical landmark and incision backstop 285 is provided by a posterior portion 286 of rim 96, as shown in FIG. 26. A posterior colpotomy incision 288 is performed by reference to and by making an incision over the second anatomical landmark and incision backstop 285. The posterior colpotomy incision 288 is performed similar to the anterior colpotomy incision 264 and is made laterally up to but short of the lateral vaginal angles 276 on both sides 276A and 276B.

Although in the preferred practice, the anterior colpotomy incision 264 is made before the posterior colpotomy incision 288, the order may be reversed.

Uterine Vessel/Cardinal Ligament Pedicle

After anterior incision 264 and posterior incision 288 have been made, the uterine vessels 292, with appropriate uterine manipulation, can be made visible and desiccated just at the level of the lateral fornix 296 as indicated by the fornix-engaging rim 96 and the anterior and posterior colpotomy incisions 264 and 288, respectively. With the elevation of the uterus 130 in the anteverted position 162, the ureters 228 are now more than 2 cm inferior and lateral to the uterine vessel oblique cardinal pedicle 300 that will now be secured with bipolar desiccation or suture ligation.

Figure 29:
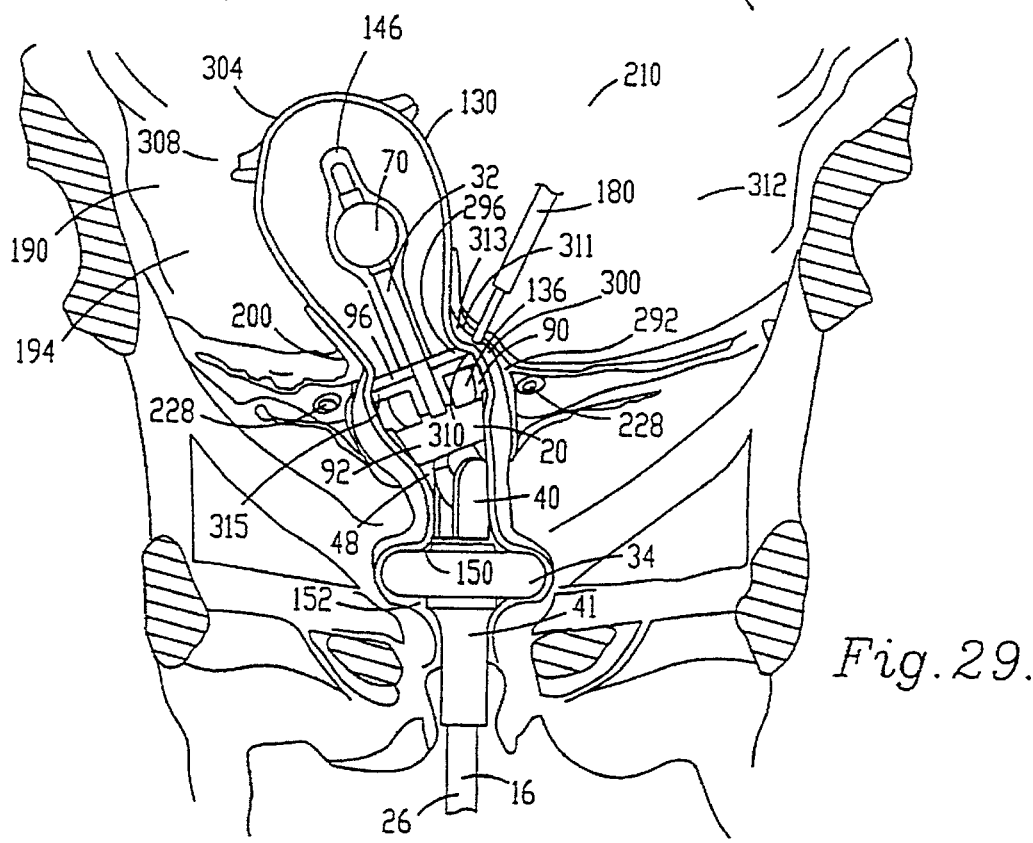
FIG. 29 is a top plan, cross-sectional view of the abdominal cavity showing the fundus moved against the inner pelvic wall.

To perform the desiccation of the uterine vessels 292 and colpotomy of the cardinal pedicle 300 located at the lateral vaginal angle 276A, as shown in FIG. 29, the uterus fundus 304 is positioned as needed towards the opposite pelvic side wall 308, which delineates the third anatomical landmark and incision backstop 310 created by a first lateral rim portion 311. The uterine vessels 292 are now visible and are bipolar desiccated at the level of the vaginal fornix apex 140 as indicated by the third anatomical landmark and incision backstop 310 and by the anterior and posterior colpotomy incisions 264 and 288, respectively. Following this the uterine vessels 292 are divided. The cardinal ligament zone 313 presented by the divided uterine vessels 292 can now be easily and safely divided, as shown in FIG. 29. The lateral vaginal angle 276A is now incised, joining the corresponding ends of the anterior and posterior colpotomy incisions 264 and 288, respectively.

The same procedure as that explained above for the incision at lateral vaginal angle 276A is performed on the opposite lateral vaginal angle 276B after first manipulating fundus 304 as needed towards the pelvic side wall 312 opposite lateral vaginal angle 276B. Once the fundus 304 is so positioned, a fourth anatomical landmark and incision backstop 314 is presented by second lateral rim 315. After the vaginal lateral angle 276B is incised, the uterus 130 is totally free in the abdominal cavity 194 and held only by the colpotomy assembly 10.

Removal of Uterus

The vaginal occluder 41 is now deflated and the colpotomy assembly 10 removed through the vagina 280. A tenaculum may be used on the cervix 136 to aid in pulling out an enlarged uterus 130. The colpotomy assembly 10, with the vaginal extender 20, tip 32, and tip base 33 removed, may be reintroduced into the vagina 280 to provide vaginal manipulation and pneumo-occlusion while vaginal closure takes place abdominally. Alternatively, vaginal closure may take place vaginally at this stage.

Closure of the Vagina

The vaginal cuff 318 can be closed by any method known in the surgical arts, including the use of three mattress sutures laparoscopically, using intracorporeal tying (not shown). The right vaginal angle 276A is secured in the mattress suture that incorporates the cardinal pedicle 300 and is tied anteriorly. The left vaginal angle 276B is similarly secured. The center of the vaginal cuff 318 is then secured with a single mattress suture and tied anteriorly. Any bleeding points are bipolar desiccated without fear of releasing the sutures as they are under the surface of the vagina 280.

If there is descent, various methods of colposuspension may be attempted. A potential enterocele may be closed, using the Moschcowitz, Halban's or McCall culdoplasty method or other variations thereof.

Laparoscopic Rescue of Vaginal Hysterectomy

While many instances of abdominal hysterectomy are performed preemptively in the belief that the vaginal hysterectomy will not succeed either from lack of decent or other complicating factors, many cases that originate vaginally are similarly converted to an abdominal hysterectomy when progress from below has ceased. The colpotomy assembly 10 and the associated method of the instant invention, however, may likewise be used to rescue a failed vaginal hysterectomy if abdominal rescue is undesirable. Such a rescue can be performed without a need of performing a laparotomy. Depending on whether the vaginal incision has been completed and whether the anterior and posterior peritoneum have been incised, the use of the vaginal extender 20 may be included or excluded. However, the use of the colpotomy assembly 10 is needed, with the vaginal extender 20, tip 32, and base 33 removed, because vaginal occluder 41 is needed for completion of the procedure.

Other Indications for Using the Colpotomy Assembly

Tissue removal may be facilitated by the use of the colpotomy assembly 10. The rim 96 of the colpotomy assembly 10 delineates the position for incising the fornix 142 for hysterectomy. When a colpotomy is required in the lower region of the vaginal cavity 322, an incision may be performed by the delineation of vaginal tissue by the lower margin of the annular main body 90 of vaginal extender 20. The vaginal extender 20 is configured such that an incision at the lower margin of the annular main body 90 can be made at a location far enough away from rectum to avoid injury, particularly in cases where there might be mild adherence of the rectum to the posterior fornix 326 as in endometriosis.

Rectovaginal Space Dissection with the Use of the Colpotomy Assembly

Cases of Rectovaginal endometriosis that involve the vaginal wall may be dissected satisfactorily and excision of the lesion including the posterior vaginal wall may be satisfactorily performed without difficulties associated with loss of pneumoperitoneum. The rigid posterior vaginal wall with the colpotomy assembly against it will also help dissection of the adherent rectum from the vagina. The excised endometriotic mass may also be removed through the vagina with or without a bag.

Bowel Resection Via Colpotomy

The step of bowel resection anastomosis which involves exteriorization of the proximal sigmoid loop in order to place the EEA tip may now be done through the colpotomy incision and then returned to the abdominal cavity 194 for completion of the anastomosis without the need to extend an abdominal wound.

Alternatively, the total anastomosis resection may be performed through the colpotomy incision as described by Redwine.

We claim:

1. A colpotomy assembly for use in female pelvic surgical procedures, said assembly comprising:

an elongated, rigid shaft member presenting a proximal end and a distal end, said distal end of said shaft member configured to be inserted into the vagina;

a shaft handle mounted in pivotal relationship to said proximal end;

an uterine manipulator presenting an enlarged base and an elongated, distally extending uterine manipulating tip;

means for mounting said base adjacent the distal end of said shaft member, and for opperably coupling said base and said shaft handle in order to selectively articulate said tip relative to said shaft member and in response to pivoting of said shaft handle; and a vaginal extender having structure for bearing a patient's vaginal fornix to provide an anatomical landmark for use in making colpotomy incisions from the abdominal cavity, said extender including structure for attachment thereof to said uterine manipulator so that the uterine manipulator and extender articulate in unison relative to said shaft member without translational shifting of said manipulator relative to said extender, in response to pivoting of said shaft handle.

2. A vaginal extender for use in making colpotomy incisions during female pelvic surgery, said extender comprising:

a cervix-engaging base; and fornix-engaging structure extending distally from said base, said fornix-engaging structure configured to bear against at least a portion of a patient's vaginal fornix apex to provide an anatomical landmark, said fornix-engaging structure comprising an annular body having a proximal end integral with said cervix-engaging base and presenting a substantially continuous circular fornix-engaging rim, said annular body presenting an outer, peripheral, generally cylindrical surface extending between said fornix-engaging rim and said cervix-engaging base, said cylindrical surface adjacent said base including a lower surface portion configured for use in colpotomy incisions, said peripheral surface further including at least one viewing window disposed in and extending through said outer peripheral surface to permit the viewing of a patient's cervix to facilitate proper engagement of said vaginal extender with the patient's cervix and vaginal fornix.

3. The vaginal extender of claim 2, said fornix-engaging rim being in the form of a substantially beveled circular surface.

4. The vaginal extender of claim 2, said annular main body including a laterally extending slot disposed on said outer peripheral surface for passing surgical instruments used to grip cervix tissue during engagement of said vaginal extender with a patient's cervix and vaginal fornix.

5. A vaginal extender for use in making colpotomy incisions during female pelvic surgery, said extender comprising:

a cervix-engaging base including a socket; and fornix-engaging structure including an annular main body extending distally from said base, said fornix-engaging structure configured to bear against at least a portion of a patient's vaginal fornix apex to provide an anatomical landmark, said cervix-engaging base including a floor portion having an aperture therethrough for communicating said socket with said annular main body, said aperture configured to permit the insertion therethrough of the uterine tip associated with an articulating uterine manipulator.

6. The vaginal extender of claim 1, said aperture having a diameter substantially greater than the diameter associated with the uterine tip to provide a view of the cervix for proper engagement by the extender of the patient's cervix and vaginal fornix during installation of the extender.

7. A vaginal extender for use in making colpotomy incisions during female pelvic surgery, said extender comprising:

a cervix-engaging base including a proximal end presenting a socket for captive engagement of a uterine tip base portion of an articulated uterine manipulator;

said socket including a floor portion having an aperture therethrough, said aperture communicating said socket with said annular main body, said aperture configured to provide a view of the cervix for proper engagement by the extender of the patient's cervix and vaginal fornix during installation of the extender;

fornix-engaging structure extending distally from said base, said fornix-engaging structure configured to bear against at least a portion of a patient's vaginal fornix apex to provide an anatomical landmark and an incision backstop, said fornix-engaging structure being in the form of an annular main body having a proximal end integral with said cervix-engaging base, and a distal end presenting a substantially continuous circular fornix-engaging rim, said rim being in the form of a substantially circular, beveled surface;

said main body presenting an outer peripheral, generally cylindrical surface extending between said fornix-engaging rim and said cervix-engaging base, said peripheral cylindrical surface adjacent said base including a lower surface portion configured for use in colpotomy incisions in a patient's intermediate vaginal wall;

at least one viewing window disposed in and extending through said outer peripheral surface to permit the viewing of the patient's cervix during the engagement of said vaginal extender with the patient's cervix and vaginal fornix; and a laterally extending slot disposed on said cylindrical peripheral surface for passing surgical instruments used to grip cervix tissue during engagement of vaginal extender with a patient's cervix and vaginal fornix.

8. The colpotomy assembly of claim 1, further comprising a vaginal occluder mounted in surrounding relationship to said shaft member proximal to said distal end, said vaginal occluder including an outwardly extensible, inflatable balloon cuff.

9. A colpotomy assembly for use in female pelvic surgical procedures, said assembly comprising:

an elongated, rigid shaft member presenting a proximal end and a distal end, said distal end of said shaft member configured to be inserted into the vagina;

a shaft handle mounted in pivotal relationship to said proximal end;

an uterine manipulator presenting an enlarged base and an elongated, distally extending uterine manipulating tip fixedly connected to said base for articulating movement therewith;

means for mounting said base adjacent the distal end of said shaft member, and for operably coupling said base and said shaft handle in order to selectively articulate said tip relative to said shaft member and in response to pivoting of said shaft handle; and a vaginal occluder mounted in surrounding relationship to said shaft member proximal to said distal end, said vaginal occluder including an outwardly extensible, inflatable balloon cuff.

10. A colpotomy assembly as set forth in claim 2, further comprising a vaginal occluder mounted in surrounding relationship to said shaft member proximal to said distal end, said vaginal occluder including an outwardly extensible, inflatable balloon cuff.

11. A colpotomy assembly as set forth in claim 5, further comprising a vaginal occluder mounted in surrounding relationship to said shaft member proximal to said distal end, said vaginal occluder including an outwardly extensible, inflatable balloon cuff.

12. A colpotomy assembly as set forth in claim 7, further comprising a vaginal occluder mounted in surrounding relationship to said shaft member proximal to said distal end, said vaginal occluder including an outwardly extensible, inflatable balloon cuff.

* * * * *